United States Patent [19]
Saha et al.

[11] Patent Number: 5,882,905
[45] Date of Patent: Mar. 16, 1999

[54] THERMOSTABLE α-L-ARABINOFURANOSIDASE FROM *AUREOBASIDIUM PULLULANS*

[75] Inventors: Badal C. Saha, Peoria; Rodney J. Bothast, East Peoria, both of Ill.

[73] Assignee: The United States of America as represented by the Secretary of Agriculture, Washington, D.C.

[21] Appl. No.: 905,113

[22] Filed: Aug. 1, 1997

[51] Int. Cl.$^6$ .............................. C12P 19/02; C12P 7/08; C12N 9/24; C12N 9/26; C12N 1/06

[52] U.S. Cl. .................. 435/105; 435/163; 435/200; 435/201; 435/255.1; 435/911

[58] Field of Search ................... 435/200, 201, 435/255.1, 911, 105, 163

[56] References Cited

U.S. PATENT DOCUMENTS 5,491,087 2/1996 Zamost et al. ......................... 435/200
5,688,161 11/1997 Rosenberg et al. .................... 435/200

OTHER PUBLICATIONS

Myburgh et al. (1991a) J. Ferm. Bioeng., 72(2), "Production of Xylan–Hydrolyzing by Enzymes *Aureobasidium pullulans*", pp. 135–137.

Myburgh et al. (1991b) Proc. Biochem., 26(6), "The Temperature and pH Properties of the Extracellular Hemicellulose–Degrading Enzymes of *Aureobasidium pullulans* NRRL Y 2311–1", pp. 343–348.

Bastawde et al. (1994). J. Indust. Microbiol., 64(1), "Purification and Characterization of a Novel Thermostable α–L–Arabinofuranosidase from a Color–Variant Strain of *Aureobasidium pullulans*", pp. 216–220.

Saha et al. (1998) Appl. Environ. Microbiol., 64(1), "Purification and Characterization of a Novel Thermostable α–L–Arabinofuranosidase from a Color–Variant Strain of *Aureobasidium pullulans*", pp. 216–220.

Biely et al. (1997) Folia Microbiol., 41(3), "Relation Between the Production of Xylanases and Mannanases in *Aureobasidium pullulans*", p. 278.

*Primary Examiner*—Jon P. Weber
*Attorney, Agent, or Firm*—M. Howard Silversein; Randall E. Deck; John D. Fado

[57] ABSTRACT

An α-L-arabinofuranosidase enzyme which is highly thermostable, and is effective for the hydrolysis of arabinofuranosyl residues from L-arabinose containing polysaccharides and hemicelluloses is disclosed. The enzyme is produced by color variant *Aureobasidium pullulans* strain NRRL Y-21792. This α-L-arabinofuranosidase may be used in conjunction with xylanolytic enzymes for the treatment of hemicellulosic materials to produce fermentable sugars, particularly xylose and L-arabinose.

13 Claims, 5 Drawing Sheets

THERMOSTABLE α-L-ARABINOFURANOSIDASE FROM *AUREOBASIDIUM PULLULANS*

BACKGROUND OF THE INVENTION

1. Field of the Invention

This invention relates to an α-L-arabinofuranosidase effective for hydrolyzing arabinosyl residues from L-arabinose containing polysaccharides and hemicelluloses, and which is stable at high temperatures.

2. Background of the Invention

More than one billion gallons of ethanol are produced annually in the United States, with approximately 95% derived from fermentation of corn starch (Bothast, 1994, Genetically engineered microorganisms for the conversion of multiple substrates to ethanol, Proc. Corn Utilization Conf., National Corn Growers Assoc., St. Louis, Mo.). Various lignocellulosic agricultural residues such as corn fiber, corn stover, straw and bagasse can also serve as low-value and abundant feedstocks for production of fuel alcohol. Currently, the utilization of lignocellulosic biomass to produce fuel ethanol presents significant technical and economic challenges, and its success depends largely on the development of highly efficient and cost-effective biocatalysts for conversion of pretreated biomass to fermentable sugars.

Hemicelluloses, the second most common polysaccharides in nature, represent about 20–35% of lignocellulosic biomass (Wyman, 1994, Bioresourc. Technol., 50:3–16). L-Arabinosyl residues are widely distributed in hemicelluloses as they constitute monomeric and/or oligomeric side chains on the β-(1→4)-linked xylose or galactose backbones in xylans, arabinoxylans and arabinogalactans, and are the core in arabinans forming α-(1→5)-linkages (Manin et al., 1994, Biochem. J., 302:443–449; Ward and Moo-Young, 1989, CRC Crit. Rev. Biotechnol., 8:237–274). These side chains restrict the enzymatic hydrolysis of hemicelluloses by xylanases (Bachmann and McCarthy, 1991, Appl. Environ. Microbiol., 57:2121–2130). α-L-Arabinofuranosidases (α-L-arabinofuranoside arabinofuranohydrolase, EC 3.2.1.55, α-L-AFase) are exo-type enzymes which hydrolyze terminal non-reducing α-L-arabinofuranosyl groups from L-arabinose containing polysaccharides. These enzymes can hydrolyze (1→3)- or (1→5) -α-L-arabinofuranosyl linkages of arabinan or both. The α-L-AFases are part of microbial xylanolytic systems necessary for complete breakdown of heteroxylans (Bachmann and McCarthy, 1991, ibid; Greve et al., 1984, Appl. Environ. Microbiol., 47:1135–1140; Lee and Forsberg, 1987, Can. J. Microbiol., 33:1011–1016; Poutanen, 1988, J. Biotechnol., 113:15–22).

In recent years, arabinofuranosidases have received much attention because of their practical applications in various agro-industrial processes such as efficient conversion of hemicellulosic biomass to fuels and chemicals, delignification of pulp, efficient utilization of plant materials into animal feed, and hydrolysis of grape monoterpenyl glycosides during wine fermentation (Bezalel et al., 1993, Appl. Environ. Microbiol., 40:57–62; Gilead and Shoham, 1995, Appl. Environ. Microbiol., 61:170–174; Gunata et al., 1990, J. Agric. Food Chem., 38:772–776; Utt et al., 1991, Appl. Environ. Microbiol., 57:1227–1234). There is a need to develop a suitable α-L-AFase for use in the conversion of hemicellulose to fermentable sugars for the subsequent production of fuel ethanol and other value-added chemicals. α-L-AFases are produced by several bacteria and fungi but only a few of these enzymes have been purified and characterized (Gilead and Shoham, ibid; Hespell and O'Bryan, 1992, Appl. Environ. Microbiol., 58:1082–1088; Kaji and Tagawa, 1970, Biochim. Biophys. Acta, 207:456–464; Lee and Forsberg, ibid; Tajana et al., 1992, Appl. Environ. Microbiol.; 58:1447–1450). The yeast-like fungus *Aureobasidium pullulans* has been recognized as an excellent producer of amylases, xylanase and β-glucosidase (Leathers, 1986, Appl. Environ. Microbiol., 52:1026–1030; Saha et al., 1993, Curr. Microbiol., 26:267–273; Saha et al., 1994, Appl. Environ. Microbiol., 60:3774–3780).

SUMMARY OF THE INVENTION

We have now discovered a new thermostable α-L-arabinofuranosidase enzyme which is effective for the hydrolysis of arabinofuranosyl residues from L-arabinose containing polysaccharides and hemicelluloses at high temperatures. The enzyme is produced by color variant *A. pullulans* strain NRRL Y-21792. This α-L-arabinofuranosidase may be used in conjunction with xylanolytic enzymes for the treatment of hemicellulosic materials to produce fermentable sugars, particularly xylose and L-arabinose.

In accordance with this discovery, it is an object of this invention to provide a novel α-L-arabinofuranosidase enzyme for the enzymatic hydrolysis of L-arabinose containing polysaccharides or hemicellulose, which is highly thermostable.

Another object of this invention is to provide an improved process for the enzymatic conversion of hemicellulose to L-arabinose using an α-L-arabinofuranosidase insensitive to high temperatures.

Another object of this invention is to provide an improved process for the enzymatic conversion of hemicellulose to L-arabinose, which may be subsequently fermented to ethanol, using an α-L-arabinofuranosidase insensitive to high temperatures.

Other objects and advantages of this invention will become readily apparent from the ensuing description.

DETAILED DESCRIPTION OF THE INVENTION

Figure 1:
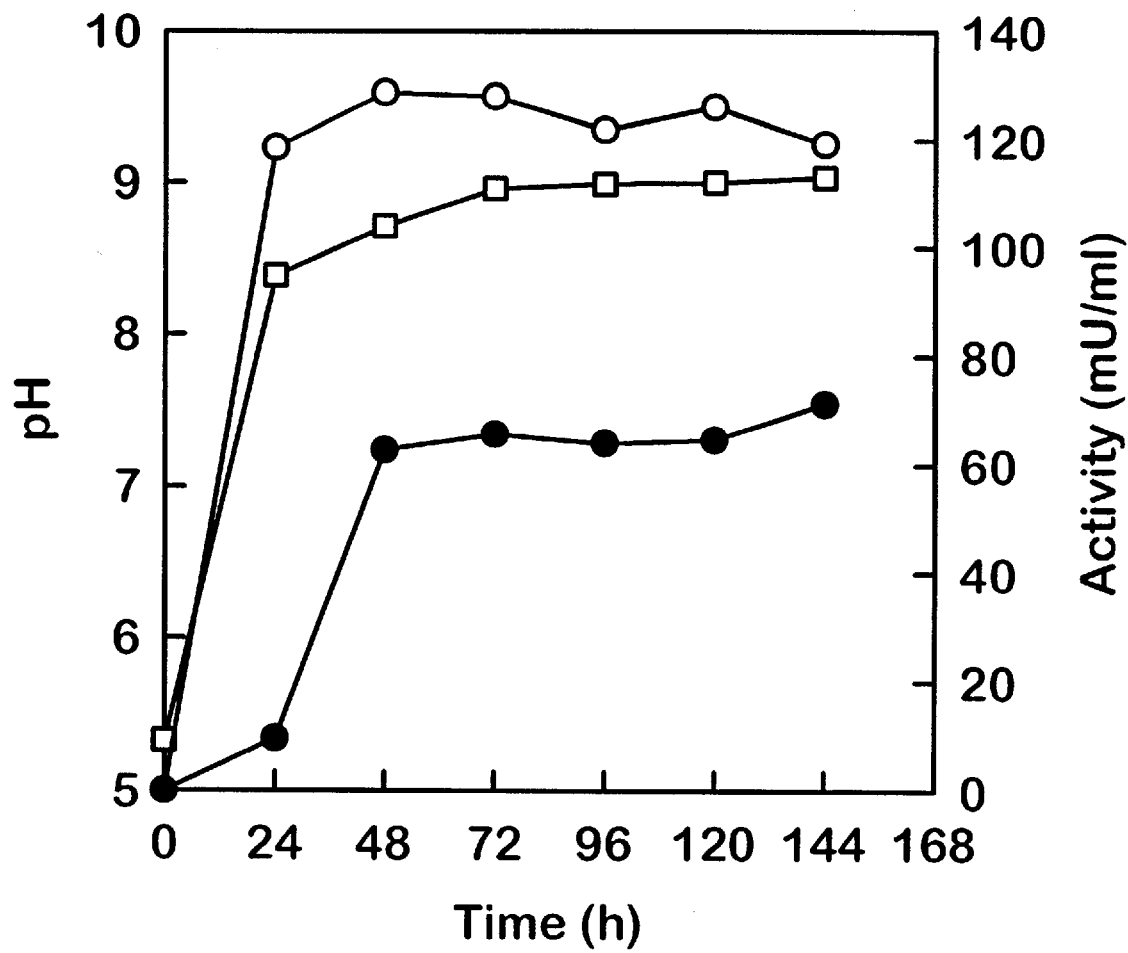
FIG. 1. Time course of α-L-arabinofuranosidase production by *A. pullulans* Y-21792 grown on oat spelt xylan (1%, w/v) at 28° C. Symbols: □, pH; ○, total α-L-arabinofuranosidase activity; ●, extracellular α-L-arabinofuranosidase activity. Values are averages of duplicate experiments.

The enzyme of this invention is an α-L-arabinofuranosidase (α-L-arabinofuranoside arabinofuranohydrolase, EC 3.2.1.55) which is effective for the exo-hydrolysis of L-arabinose containing polysaccharides and hemicelluloses with the release of L-arabinose (α-L-arabinofuranose) therefrom. A variety of L-arabinose containing substrates may be hydrolyzed by the enzyme, including but not limited to, xylans, arabinoxylans, and arabinan. The enzyme possesses specific hydrolytic activity for both the (1→3)- and (1→5)-linked, terminal non-reducing α-L-arabinofuranose residues from any L-arabinose containing polysaccharide or hemicellulose, and does not act on any internal α-L-arabinosyl linkages.

Surprisingly, the purified α-L-arabinofuranosidase of this invention is highly thermophilic, displaying optimal activity at 75° C. and pH 4.0–4.5, and having a half life of 8 hours, at 75° C. The specific activity of the enzyme is 21.48 U/mg at pH 4.5 and 75° C. The enzyme exhibits substantially no inhibition of activity at L-arabinose (α-L-arabinofuranose) concentrations less than or equal to about 21.6% (1.2M).

The preferred microorganism for the production of the α-L-arabinofuranosidase of this invention is a strain of *Aureobasidium pullans*, strain NRRL Y-21792. The strain was deposited under the Budapest Treaty in the Agricultural Research Service Culture Collection in Peoria, Ill., on Jun. 24, 1997. This same strain of *Aureobasidium pullulans* is also available from the general collection of the Agricultural Research Service Culture Collection under accession number NRRL Y-12974.

*Aureobasidium pullulans* strain NRRL Y-21792 used in this invention is a color variant strain of *A. pullulans*. The morphological and carbon assimilation patterns for this strain are typical for this species as described by Barnett and Hunter (Illustrated Genera of Imperfect Fungi, Burgess Publishing, Minneapolis, Minn., 1972, pp. 64–65) and in The Yeasts, A Taxonomic Study (fourth edition, Kurtzman and Fell [ed.], Elsevier Science B. V., 1997, pp. 920–921), the contents of each of which are incorporated by reference herein. The strain is differentiated from typical strains of *A. pullulans* by its brilliant pink pigment, overproduction of xylanase, and low DNA relatedness (Leathers et al, 1988, J. Indust. Microbiol., 3:231–239).

Morphologically, mycelia are not extensive, are hyaline when young, becoming dark with age, black and shiny in old cultures, and bear abundant lateral conidia. Conidia are subhyaline to dark, 1-celled, ovoid, and produce other conidia by budding. Colonies are yeast like and produce a bright pink pigment on yeast extract-malt extract medium (YM). The strain is unable to ferment any of glucose, galactose, sucrose, maltose, lactose, raffinose, or trehalose. A wide range of carbon sources are assimilated, including: glucose, galactose, L-sorbose, sucrose, maltose, cellobiose, trehalose, melibiose, raffinose, melezitose, inulin, soluble starch, D-xylose, L-arabinose, D-ribose, L-rhamnose, D-glucosamine, ethanol, glycerol, erythritol, ribitol, D-mannitol, D-glucitol, D-gluconate, and inositol. Nitrate is assimilated and gelatin is liquefied.

For the purposes of this invention, any isolate of *Aureobasidium pullulans* having the identifying characteristics of strain NRRL Y-21792, including subcultures and variants thereof which retain the ability to produce highly thermostable α-L-arabinofuranosidase, are effective for use herein. The term variant is defined herein to include transformants and mutants of *Aureobasidium pullulans* which are capable of producing the enzyme. For example, without being limited thereto, artificial variants of the strain may be produced by conventional treatment with various known mutagens, such as UV rays, X-rays, high frequency waves, radioactive waves, and chemical mutagens such as nitrous acid, and N-methyl-N'-nitro-N-nitrosoguanidine.

Production of the α-L-arabinofuranosidase may be accomplished by culture of the aforementioned *A. pullulans* isolates, using conventional techniques under aerobic conditions that are effective to promote growth and α-L-arabinofuranosidase production. Any number of well-known liquid or solid nutrient culture media may be used, although growth on liquid media is preferred as a substantial portion the enzyme is extracellular and secreted into the media where recovery is simplified. The carbon source used in the media should be effective for inducing production of the α-L-arabinofuranosidase. A variety of carbon sources are suitable for use herein, and include but are not limited to L-arabinose, L-arabitol, arabinan, arabinoxylan, xylose, xylitol, oat spent xylan, and, to a lesser extent, arabinogalactan and corn fiber. However, optimal enzyme production has been obtained using L-arabinose at low concentrations (i.e., about 1t w/v). The fungus will grow and produce the α-L-arabinofuranosidase over wide pH and temperature ranges, with a pH of about 5.0 and a temperature between about 25–30° C. being preferred.

Under these cultivation conditions, optimal production of α-L-arabinofuranosidase is achieved between about 48 to 96 hours, after which time enzyme production decreases gradually. Upon completion of the fermentation the α-L-arabinofuranosidase may be isolated or separated from the cells using techniques conventional in the art, such as by centrifugation or filtration.

As a practical matter, it is envisioned that commercial formulations of the α-L-arabinofuranosidase may be prepared directly from liquid culture medium from which cells have been removed in the above-described manner, thereby obviating the need to further purify the enzyme. However, in an alternative embodiment, the α-L-arabinofuranosidase remaining in the culture medium may be further concentrated and purified, particularly for applications demanding a high degree of purity where contamination by other enzymes, microbial products, or culture media components may be undesirable. Concentration and/or purification of the α-L-arabinofuranosidase may be effected by use of conventional techniques, including, but not limited to, ultrafiltration, dialysis, ion-exchange chromatography, HPLC, size-exclusion chromatography, arabinan-sepharose affinity chromatography, and electrophoresis, such as polyacrylamide-gel-electrophoresis (PAGE). Using these techniques, α-L-arabinofuranosidase may be recovered in pure or substantially pure form. It is also envisioned that the enzyme may be formulated in conjunction with a suitable inert carrier or vehicle as known in the art. The skilled practitioner will recognize that such carriers must be compatible with the enzyme. Without being limited thereto, details of the preferred fermentation and separation procedures are described in the Examples.

The α-L-arabinofuranosidase may be used alone, or preferably in combination with one or more other xylanolytic enzymes, for the hydrolysis of L-arabinose (L-arabinofuranose) containing polysaccharides or hemicelluloses. Examples of hemicellulosic materials which may be treated in accordance with this invention include lignocellulosic biomass such as agricultural residues (straws, hulls, stems, stalks), corn fiber, wood, municipal solid wastes (paper, cardboard, yard trash, and wood products), wastes from the pulp and paper industry, and herbaceous crops. Specific applications of the enzyme include, but are not limited to, the saccharification of L-arabinose containing polysaccharides and hemicelluloses to fermentable sugars L-arabinose and xylose for subsequent fermentation to ethanol or arabitol, the treatment of plant materials for use as animal feed, delignification of pulp, hydrolysis of grape monoterpenyl glycosides during wine fermentation, and clarification and thinning of juices.

When used alone, the enzyme effectively exohydrolytically cleaves the substrate with the release of L-arabinose therefrom. The resultant L-arabinose and/or hydrolyzed substrate may be recovered and subsequently used in a variety of applications, or they may be subjected to additional treatments. Where a greater degree of hydrolysis or saccharification is required, particularly for the treatment of hemicelluloses, the α-L-arabinofuranosidase is preferably used in combination with one or more xylanolytic enzymes. A variety of xylanolytic enzymes are suitable for use herein, and the specific enzyme selected will vary with the substrate and the desired degree of hydrolysis. Without being limited thereto, particularly preferred enzymes which may be used in combination with α-L-arabinofuranosidase include endoxylanase (endo-1,4-β-xylanase) which hydrolyzes the linear polyxylose chain of xylans and arabinoxylans to xylooligosaccharides and xylobiose, and β-xylosidase which hydrolyzes the xylobiose and oligosaccharides to complete the conversion of xylan to xylose.

Optimal hydrolysis of the hemicellulosic materials to both fermentable sugars L-arabinose and xylose is achieved when the α-L-arabinofuranosidase is used in combination with one or both endoxylanase and β-xylosidase. Left intact, L-arabinose side chains in hemicelluloses restrict the enzymatic hydrolysis of the substrates by endoxylanase and β-xylosidase. However, treatment of the hemicellulosic materials with the α-L-arabinofuranosidase cleaves the L-arabinose side groups from the substrate, significantly increasing the subsequent hydrolysis of the substrate by the endoxylanase and β-xylosidase. Still other xylanolytic enzymes which are effective for removing side groups from polymeric xylans and which may be used herein include ferulic acid esterase, α-glucuronidase, acetyl xylan esterase, and p-coumaroyl esterase.

The source of the xylanolytic enzymes is not critical, and suitable enzymes may be obtained from commercial preparations, or they may be produced by culture of well known microorganisms, most notably Aureobasidium, Thermomonospora, and Streptomyces species, such as described by Sunna and Antranikan (1997, Critic. Rev. in Biotech., 17(1):39–67), Ball and McCarthy (1988, J. Gen Microbiol., 134:2139–2147) or Bachmann and McCarthy (1991, Appl. Environ. Microbiol., 57:2121–2130), the contents of each of which are incorporated by reference herein.

Hydrolysis of the hemicellulosic materials may be accomplished using conventional techniques. A number of processes have been described for the enzymatic hydrolysis of lignocellulosic materials generally using cellulolytic and/or xylanolytic (hemicellulase) enzymes, and are suitable for use with the enzymes described herein as well. These include, but are not limited to, techniques described by Hespell et al. (1997, Appl. Biochem. Biotechnol., 62:87–97), and techniques reviewed by Wright (1988, Chem. Engin. Progress, 84(8):62–74), the contents of each of which are incorporated by reference herein.

In general, the L-arabinose containing substrate material is contacted with catalytically effective amounts of the α-L-arabinofuranosidase and optional xylanolytic enzymes in an aqueous solution and under conditions effective to first hydrolyze L-arabinose from the substrate, and then hydrolyze the remaining substrate to xylose. The substrate may be treated with the enzymes in combination (concurrently), although optimal hydrolysis of the entire substrate may require sequential (consecutive) treatment with the α-L-arabinofuranosidase applied first, followed by xylanase and then xylosidase. Sequential treatment with the enzymes in this manner will allow the reaction conditions (e.g., temperature and pH) to be selected in accordance with the optima for each enzyme.

The actual amount of the enzymes and the conditions for the reaction will vary with the substrate and the source of the xylanolytic enzymes, and may be readily determined. Optimal pH and temperature conditions for the α-L-arabinofuranosidase, are about 4.0–4.5 and 75° C., respectively. However, optimal conditions for the xylanolytic enzymes may be different. Typically, for optimal xylanase activity, the pH will be between about 4.0 to 9.0, and the temperature will be between about 40 to 80° C. (Sunna and Antranikian, 1997, ibid); and Ball and McCarthy, 1988, ibid). Owing to the thermostability tolerance of the novel α-L-arabinofuranosidase, the temperature of the reaction may be higher than processes which have been previously described.

The process may be conducted with agitation in conventional batch, fed-batch, or continuous reactor systems, such as described by Wang et al. (1979, Fermentation and Enzyme Technology, John Wiley & Sons, New York, pp. 339–343). Furthermore, the enzymes may be in solution or, in the alternative, immobilized onto a conventional solid support. A number of techniques for the immobilization of enzymes have been previously reported and may be used with the enzyme of this invention as well. Examples of suitable immobilization techniques and supports include, but are not limited to, those described by Woodward and Capps (1992, Appl. Biochem. Biotechnol., 34/35:341–347), Karube et al. (1977, Biotech. Bioeng., 19:1183–1191), Woodward and Zachry (1982, Enzyme Microb. Technol., 4:245–248), Srinivasan and Bumm (1974, Biotech. Bioeng., 16:1413–1418), Bissett and Sternberg (1978, Appl. Environ. Microbiol., 35:750–755), Venardos et al. (1980, Enzyme Microb. Technol., 2:112–116), and Sundstrom et al. (1981, Biotechnol. Bioeng., 23:473–485), the contents of each of which are incorporated by reference herein. If the enzymes are in solution, they may be optionally recovered from the product stream for recycle, such as described by Lee et al. (1995, Biotechnol. Bioeng., 45:328–336), the contents of which are also incorporated by reference herein.

This invention may be practiced using lignocellulosic biomass as the substrate. While it is envisioned that this biomass may be treated with the enzymes directly, the rate of hydrolysis and fermentable sugar yields will be significantly reduced due to the complex structure of these molecules preventing enzyme access to the hemicellulose. Consequently, in the preferred embodiment, the lignocellulosic biomass is pretreated to break down the lignin-hemicellulose matrix, solubilizing the hemicellulose and/or increasing the surface area of hemicellulose accessible to the enzymes. The advantages of pretreating lignocellulosic biomass in this manner have been widely recognized in the art, and a variety of different mechanical and chemical pretreatments have been described. Examples of pretreatments which may be suitable for use herein include, but are not limited to treatment with dilute or concentrated acid (e.g., HCl, $H_2SO_4$, or $H_3PO_4$) treatment with alkali (e.g., NaOH, or $NH_4OH$) or alkaline peroxide, ammonia fiber (or freeze) explosion (AFEX), treatment with organic solvents (e.g., ethanol, methanol, ethylene glycol, butanol, phenol), autohydrolysis by steam explosion, acid steam ($SO_2$) treatment, treatment with hot, compressed liquid water, or pressure cooking. Mechanical pretreatments which may be used include ball or roll milling, grinding, shearing, or extruding. A detailed review of the mechanisms and conditions for these different pretreatments is described by McMillan (Pretreatment of Lignocellulosic Biomass, In: *Enzymatic Conversion of Biomass for Fuels Production*, Himmel et al. [ed.], American Chemical Soc., Washington, D.C., 1994, pp. 293–324), Weil et al. (1994, Enzyme Microb. Technol., 16:1002–1004), and Wright (1988, ibid), the contents of each of which are incorporated by reference herein.

The above-described pretreatments vary considerably in their effectiveness and in the physical and chemical properties of the resultant, treated substrates. For instance, acid pretreatments often produce furfural or other compounds which are toxic to many microorganisms. Before the hydrolyzed substrate may be subjected to any subsequent fermentation, these toxic compounds must be removed, such as by vacuum distillation, and the acid must be neutralized (Dunning and Lathrop, 1945, Indust. Eng. Chem., 37:24–29). Furthermore, the pretreatment itself may result in the hydrolysis of a portion of the hemicellulose to oligomers, or the saccharides xylose and L-arabinose. The actual degree of hydrolysis will vary greatly with the particular pretreatment selected. For instance, hemicellulose hydrolysis resulting from pretreatment with ammonia freeze explosion, alkali, or organic solvents is typically very small. In contrast, pretreatment of lignocellulosic substrates with acids, particularly concentrated acids and/or acids at high temperatures, generally hydrolyzes a large portion of the hemicellulose to sugars. Still other pretreatments (i.e. steam explosion) may result in the loss of large amounts of sugars.

In view of the differences between the pretreatments, the selection of the optimal procedure will vary with the particular substrate and the desired application or further treatment of the hydrolyzed substrate and sugars. However, pretreatments which are typically preferred for use herein include treatment with organic solvents (e.g., ethanol, methanol, ethylene glycol, butanol, phenol), treatment with alkali (e.g., NaOH, $NH_4OH$, or alkaline peroxide), and ammonia fiber (or freeze) explosion (AFEX). Low temperature AFEX pretreatment as described by Bothast et al. (Conversion of Corn Fiber to Ethanol, In: *Liquid Fuel and Industrial Products from Renewable Resources*, Cundiff et al. [ed.], The American Society for Agricultural Engineers, St. Joseph, Mich., 1996, pp. 241–252), Hespell et al. (1997, ibid) and DeLaRosa et al. (1994, Appl. Biochem. Biotechnol., 45/46:483–497), the contents of each of which are incorporated by reference herein, is particularly preferred.

At the conclusion of the pretreatment of the lignocellulosic material, the solid residue will typically contain cellulose and lignin. All or a portion of the hemicellulose may be solubilized into the liquid phase, as in the case of chemical pretreatments such as AFEX, acid, base, solvent, or steam treatments, or it may remain entirely in the solid phase as in the case of mechanical treatments. The cellulose containing fraction may be retained for enzymatic conversion to glucose as described by Saha and Bothast (U.S. patent application Ser. No. 08/691,757, filed Aug. 2, 1996), Olsson and Hahn-Hägerdal (1996, Enzyme Microbial Technol., 18:312–331), or Wright (1988, ibid), the contents of each of which are incorporated by reference herein.

The hemicellulose containing fraction from the pretreatment is retained for enzymatic conversion to L-arabinose and/or xylose using the α-L-arabinofuranosidase of this invention as described above. Following completion of this enzymatic hydrolysis, the L-arabinose may be recovered and stored, or it may be subsequently fermented to ethanol using conventional techniques.

Processes for the fermentation of L-arabinose are known in the art, and are suitable for use herein. In brief, the hydrolyzate containing the L-arabinose from the enzymatic reaction is contacted with an appropriate microorganism under conditions effective for the fermentation of the L-arabinose to ethanol. This fermentation may be separate from and follow the enzymatic hydrolysis of the L-arabinose containing substrate (sequentially processed), or the hydrolysis and fermentation may be concurrent and conducted in the same vessel (simultaneously processed). Without being limited thereto, preferred microorganisms include recombinant *Escherichia coli* containing the genes encoding pyruvate decarboxylase and alcohol dehydrogenase from *Zymomonas mobilis* (e.g. *E. coli* strains ATCC 8677, ATCC 8739, ATCC 9637, ATCC 11303, ATCC 11775, ATCC 14948, ATCC 15224, ATCC 23227, and strains SL40, and KO11) as described by Ingram et al. (U.S. Pat. No. 5,000, 000), Ohta et al. (1991, Appl. Environment. Microb., 57:893–900), and Lindsay et al. (1995, Appl. Microbiol. Biotechnol., 43:70–75), the contents of each of which are incorporated by reference herein. Still other suitable microorganisms include *Ambrosiozyma monospora* NRRL Y-1484, *Candida* sp. NRRL YB-2248, *Candida auringiensis* NRRL Y-11848, and *Candida succiphila* NRRL Y-11998, as described by Dien et al. (1996, Appl. Biochem. Biotechnol., 57/58:233–242), and recombinant *Zymomonas mobilis* described by Deanda et al. (1996, Appl. Environ. Microbial., 62:4465–4470), the contents of each which are incorporated by reference herein. Details of the fermentation techniques and conditions have also been described, for example, by Beall et al. (1991, Biotechnol. Bioengin., 38:296–303) and Moniruzzaman et al. (1996, Biotechnol. Lett., 18:985–990), the contents of each of which are incorporated by reference herein as well. In the preferred embodiment, the xylose may also be fermented to ethanol as described by Wyman (1994, Bioresource Technol., 50:3–16) or Olsson and Hahn-Hägerdal (1996, ibid), the contents of each of which are incorporated by reference herein.

After completion of the fermentation, the ethanol may be recovered and optionally purified or distilled. Solid residue containing lignin may be discarded or burned as a fuel.

The following examples are intended only to further illustrate the invention and are not intended to limit the scope of the invention which is defined by the claims.

EXAMPLE 1

Materials and Methods

Materials. Arabinogalactan, all saccharides, all arylglycosides and molecular weight markers for gel filtration were purchased from Sigma Chemical Co., St. Louis, Mo. Arabinan (beet sugar), debranched arabinan, wheat arabinoxylan and rye arabinoxylan were purchased from MegaZyme, North Rocks, Australia. Molecular weight markers and precast gels for SDS-PAGE, DEAE Bio-Gel A agarose, Bio Gel A-0.5m, Aminex HPX-87C column for high pressure liquid chromatography (HPLC) were obtained from Bio-Rad Laboratories, Hercules, Calif. SP-Sephadex C-50 and epoxy activated Sepharose 6B were from Pharmacia LKB Biotechnology, Piscataway, N.J.

Organism, cultivation and enzyme production. The color variant strain NRRL Y-21792 of *A. pullulans* (also available as NRRL Y-12974) was obtained from the ARS culture collection, NCAUR, Peoria, Ill. The medium used for seed culture and enzyme production was CCY medium (Slininger et al., 1982, Biotechnol. Bioeng., 23:371–384) with the following composition (g/L): 10 ml of solution A, 10 ml of solution B. 100 ml of solution C, 10 g of yeast extract and 10 g of oat spelt xylan. Solution A was a trace mineral solution having the following ingredients (per L): 1.1 g of CaO, 0.4 g of ZnO, 5.4 g of $FeCl_3.6 H_2O$, 0.25 g of $CuSO_4.5H_2O$, 0.24 g of $CoCl_2. 6H_2O$, 0.06 g of $H_3BO_3$ and 13 ml of concentrated HCl. Solution B (per L) contained 10.1 g of MgO and 45 ml of concentrated HCl. Solution C (per L) contained 64 g of urea, 12 g of $KH_2PO_4$ and 1.8 g of $Na_2HPO_4$. Oat spelt xylan was sterilized separately. The pH of the medium was adjusted to 5.0 with 1M HCl before inoculation. A 125-ml Erlenmeyer flask containing 50 ml of medium with oat spelt xylan (1%, w/v) as a carbon source was inoculated with a loopful of cells taken from a stock slant and incubated at 28° C. on a rotary shaker (200 rpm) for 2 days. The shake flasks (250-ml Erlenmeyer flask containing 100 ml medium with 1% oat spelt xylan) were inoculated with 2 ml of this culture and cultivated on a rotary shaker (200 rpm) at 28° C. After 3 days, the cells were removed from the culture broth by centrifugation (18,000×g, 20 min). The resulting supernatant solution was used as the crude enzyme preparation.

Enzyme assay. αL-arabinofuranosidase (α-L-AFase) activity was assayed in a reaction mixture (1 ml) containing 1 mM p-nitrophenyl α-L-arabinofuranoside (pNPαAF), 50 mM acetate buffer, pH 4.5 and appropriately diluted enzyme solution. After incubation at 50° C. for 30 min, the reaction was stopped by adding ice-cold 0.5M $Na_2CO_3$ (1 ml) and the color formed was measured at 405 nm. One unit (U) of α-L-AFase activity was defined as the amount of enzyme that liberates 1 μmol p-nitrophenol (pNP) per min in the reaction mixture under these assay conditions.

Purification of α-L-arabinofuranosidase. All purification steps were performed at 4° C., unless otherwise stated.

(i) Ammonium sulfate treatment. The culture supernatant (1,500 ml) was treated with ammonium sulfate (80% saturation) and left overnight. The precipitate was collected by centrifugation at 48,000×g for 30 min, dissolved in 50 mM acetate buffer, pH 5.0 and dialyzed overnight against the same buffer.

(ii) DEAE Bio-Gel A agarose column chromatography. The dialyzed enzyme solution (630 ml) was concentrated to ~20 ml by ultrafiltration with a stirred cell (model 202; Amicon, Inc., Beverly, Mass.) equipped with a PM 10 membrane under nitrogen pressure of 20 lb/in$^2$, diluted 10-fold with 50 mM imidazole buffer, pH 6.5 and applied to a DEAE Bio-Gel A agarose column (2.5×26 cm) pre-equilibrated with 50 mM imidazole buffer, pH 6.5. The column was washed extensively with the same buffer and eluted with a gradient of 0–0.5M NaCl in the same buffer (280 ml each). The α-L-AFase activity was eluted as a single peak. The highly active fractions (fractions 21–27, each fraction, 9 ml) were pooled, concentrated by ultrafiltration using PM 10 membrane, and dialyzed overnight against 50 mM acetate buffer, pH 5.0.

(iii) Gel filtration on Bio-Gel A-0.5m. The α-L-AFase was further purified by gel filtration on a Bio-Gel A-0.5m column (1.5×120 cm) pre-equilibrated with 50 mM acetate buffer, pH 5.0. The enzyme solution in 50 mM acetate buffer, pH 5.0 was applied to the column and eluted with the same buffer. The highly active α-L-AFase fractions (fractions 38–50, each fraction, 2.5 ml) were pooled and concentrated by ultrafiltration (PM 10 membrane).

(iv) Arabinan-Sepharose 6B affinity chromatography. Arabinan-Sepharose affinity matrix was prepared by coupling arabinan to epoxy-activated Sepharose 6B by the standard procedure (Affinity chromatography principles and methods, Pharmacia Fine Chemicals, Uppsala, Sweden). The α-L-AFase obtained after Bio-Gel A-0.5m gel filtration was applied to the arabinan-Sepharose 6B column (2.5×6 cm) pre-equilibrated with 50 mM acetate buffer, pH 5.0. The column was extensively washed with this buffer and the enzyme was eluted with 1M NaCl in the same buffer. The active enzyme fractions were pooled, concentrated by ultrafiltration (PM 10 membrane) and dialyzed against 50 mM citrate-phosphate buffer, pH 3.5.

(v) SP-Sephadex C-50 column chromatography. The dialyzed enzyme solution was applied to a SP-Sephadex column (2.5×10 cm) pre-equilibrated with 50 mM citrate-phosphate buffer, pH 3.5. The column was washed extensively with the same buffer and eluted with a gradient of 0–0.5M NaCl in the same buffer (150 ml each). The α-L-AFase activity was eluted as a single peak. The active enzyme fractions (each fraction, 6.4 ml) were pooled, concentrated by ultrafiltration using a PM 10 membrane and dialyzed overnight against 50 mM acetate buffer, pH 5.0. The dialyzed enzyme solution was used as purified α-L-AFase for subsequent studies.

Other methods. Protein was estimated by the method of Lowry et al. (1951, J. Biol. Chem., 193:265–275) with bovine serum albumin as the standard. Protein in the column effluents was monitored by measuring absorbance at 280 nm. Sodium dodecyl sulfate-polyacrylamide gel electrophoresis (SDS-PAGE) was performed on a 7.5% gel according to Laemmli (1970, Nature, 227:680–685). The molecular weight of the native enzyme was determined by gel filtration on Bio-Gel A-0.5m as described by Andrews (1965, Biochem. J., 91:595–606), using apoferritin (MW 443,000), sweet potato β-amylase (200,000), yeast alcohol dehydrogenase (150,000), bovine serum albumin (66,000) and ovalbumin (45,000) as standard proteins. The half-life of the enzyme was estimated by incubating the enzyme at 75° C. and determining the residual enzyme activity after certain intervals. The $K_m$ and $V_{max}$ values were determined by the double-reciprocal plot method of Lineweaver-Burk (1934, J. Am. Chem. Soc., 56:658–666) using the KINET software program. Arabinose analysis was performed by HPLC (Spectra-Physics, San Jose, Calif.) using an ion moderated partition chromatography column (Aminex HPX-87C). The column was maintained at 85° C., and the sugars were eluted with Milli-Q water at a flow rate of 0.6 ml/min. Peaks were detected by refractive index, and identified and quantified by comparison to retention times of authentic standards (L-arabinose, D-glucose, D-xylose).

Results

Production of α-L-arabinofuranosidase. The time course of α-L-AFase production by *A. pullulans* grown on oat spelt xylan is shown in FIG. 1. The extracellular α-L-AFase production increased sharply during the 24 to 48 h growth period after which it remained almost the same. The whole broth α-L-AFase activity (assayed without breaking the cells) increased sharply up to 24 h, slowly increased up to 48 h and then declined slowly. About 50% of the enzyme activity was extracellular.

Purification of α-L-arabinofuranosidase. An extracellular α-L-AFase was purified to homogeneity from the culture filtrates of *A. pullulans* grown on oat spelt xylan. A summary of the purification procedures is presented in Table 1. Only the first few active fractions with high specific activity were pooled in the case of Bio Gel A-0.5m gel filtration. The α-L-AFase was well adsorbed on the arabinan-Sepharose affinity matrix but was easily eluted with 1M NaCl. The enzyme was also well adsorbed onto the SP-Sephadex C-50 cation exchange matrix at pH 3.5. SDS-PAGE analysis of the purified α-L-AFase, indicated the presence of a single band when stained with Coomassie Brilliant Blue. The final purification resulted in a yield of 11% of the activity and 0.05% retention of total protein and a 232-fold increase in specific activity (Table 1).

Characterization of α-L-arabinofuranosidase.

The purified α-L-AFase had a specific activity of 8.59 U/mg protein (assayed at pH 4.5 and 50° C. using pNPαAF as substrate). The specific activity of the purified enzyme under optimal conditions (at pH 4.5 and 75° C.) was 21.48 U/mg protein.

Figure 2:
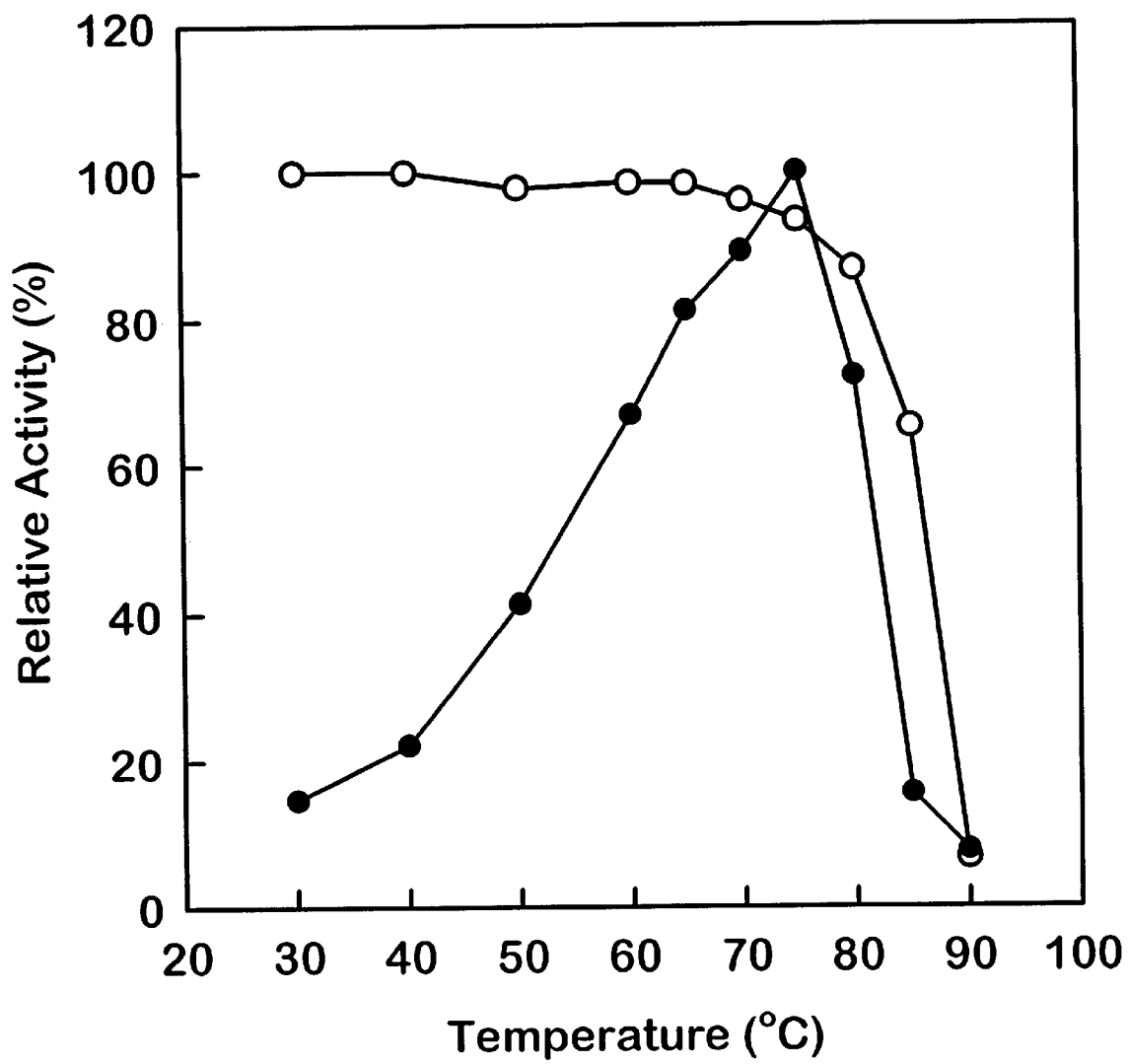
FIG. 2. Effect of temperature on stability (○) and activity (●) of purified α-L-arabinofuranosidase from *A. pullulans* Y-21792. For stability, the enzyme solution in acetate buffer (50 mM, pH 5.0) was incubated for 30 min at various temperatures, and then the residual enzyme activities were assayed. For activity, the enzyme activity was assayed at various temperatures by the standard assay method. Enzyme used, 18 mU/ml.
Figure 3:
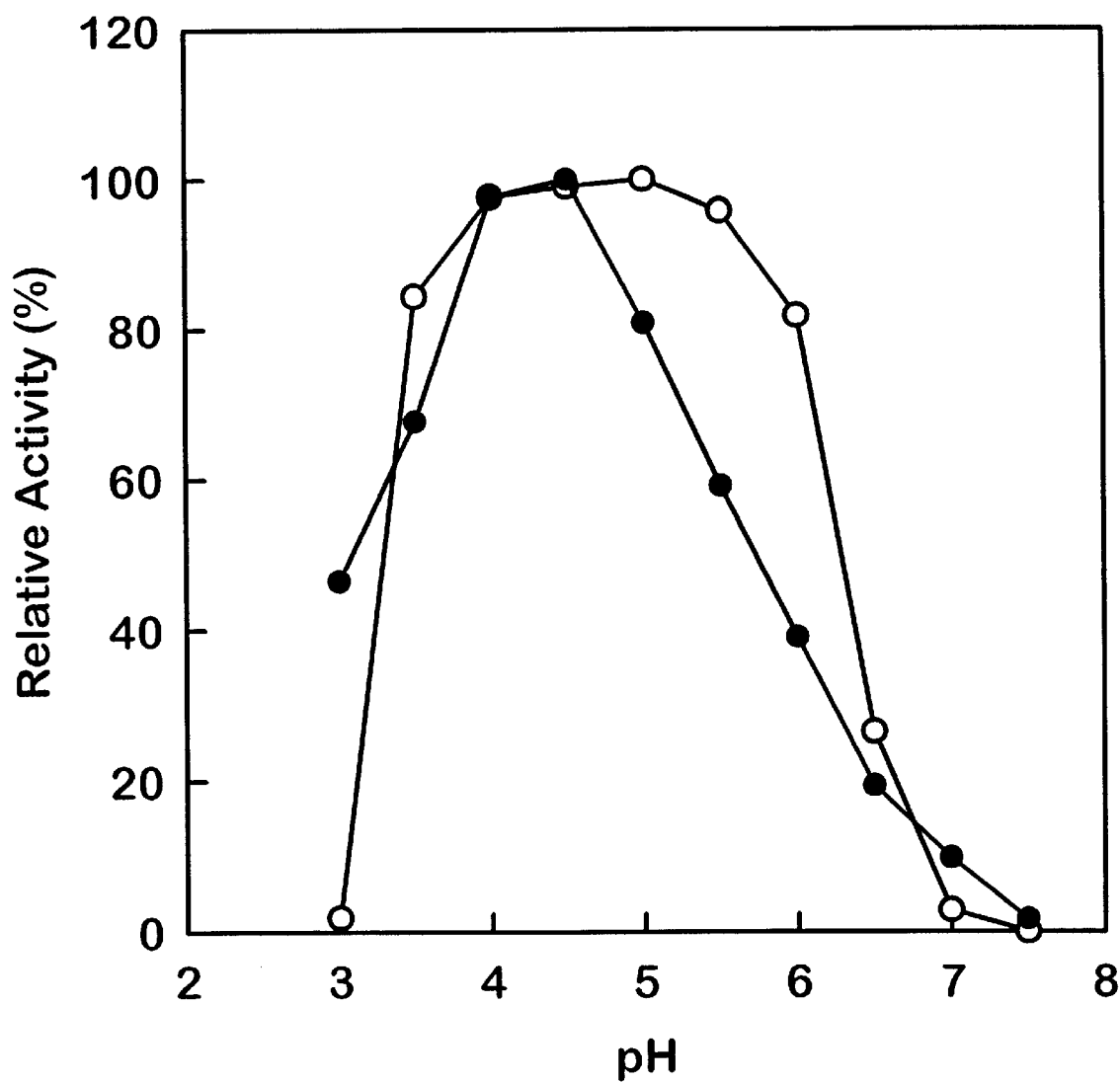
FIG. 3. Effect of pH on stability (○) and activity (●) of purified α-L-arabinofuranosidase from *A. pullulans* Y-21792. For stability, the enzyme solutions in 50 mM citrate-phosphate buffer at various pH values were incubated for 1 h at 75° C. After adjustment of pH, the residual activity was assayed by the standard method. The enzyme activity was assayed by the standard assay method by changing the buffer to obtain the desired pH. Buffer used, 50 mM citrate-phosphate, pH 3.0–8.0. Enzyme used, 18 mU/ml.

Molecular weight. The molecular weight of the native α-L-AFase estimated by gel filtration on Bio-Gel A-0.5m was 210,000. By SDS-PAGE analysis, the molecular weight of the enzyme was about 105,000, suggesting that the α-L-AFase was composed of two subunits of equal molecular weight.

pH and temperature dependence. The thermostability and thermoactivity of the purified α-L-AFase from *A. pullulans* are shown in FIG. 2. The purified enzyme in 50 mM acetate buffer, pH 5.0 (18 mU/ml; 2.11 µg protein/ml) was fairly stable up to 75° C. for 30 min with a half-life of about 8 h at 75° C. It exhibited maximum activity at 75° C. under the assay conditions used (FIG. 2). The enzyme was stable at pH 4.0–5.5 (1 h at 75° C.) (FIG. 3). It displayed an optimum activity at pH 4.0–4.5 with 47% and 40% relative activity at pH 3.0 and 6.0, respectively (FIG. 3).

Substrate specificity and kinetic analysis. Relative initial rates of hydrolysis of p-nitrophenyl-α-L-arabinopyranoside, p-nitrophenyl-β-D-glucoside, p-nitrophenyl-β-D-glucoside, p-nitrophenyl-β-D-xyloside, p-nitrophenyl-β-D-cellobioside and p-nitrophenyl-β-D-galactoside (4 mM each) by the purified α-L-AFase (28 mU/ml) were 3.4, 2.3, 1.7, 3.1, 0.0, and 0.1%, respectively (expressed as a percentage of that obtained with pNPαAF at pH 4.5 and 75° C., 15 min reaction). The rate dependence of the enzymatic reaction on the pNPαAF concentration at pH 4.5 and 75° C. followed Michaelis-Menten kinetics. Reciprocal plot showed apparent $K_m$ value of 0.26 mM and $V_{max}$ value of 6.99 µmol pNP. $min^{-1}.mg^{-1}$ protein for the hydrolysis of pNPαAF. Substrate inhibition was not observed with pNPαAF tested up to 8 mM concentration.

Effect of L-arabinose and other sugars. Up to 1.2M (21.6%) L-arabinose was not at all inhibitory to the enzyme. Xylose, glucose, mannose, galactose, xylitol and L-arabitol (each at 0.11M) did not inhibit the α-L-AFase activity.

Effect of metal ions and reagents. The influence of certain inhibitors or activators on α-L-AFase activity was studied. The enzyme did not require $Ca^{2+}$, $Mg^{2+}$, $Mn^{2+}$ (each at 5 mM) or $Co^{2+}$ (0.5 mM) for activity. Enzyme activity was not affected by ethylenediaminetetraacetate (EDTA, 10 mM), dithiothreitol (DTT, 10 mM) or by p-chloromercuribenzoic acid (pCMB, 0.2 mM).

Figure 4:
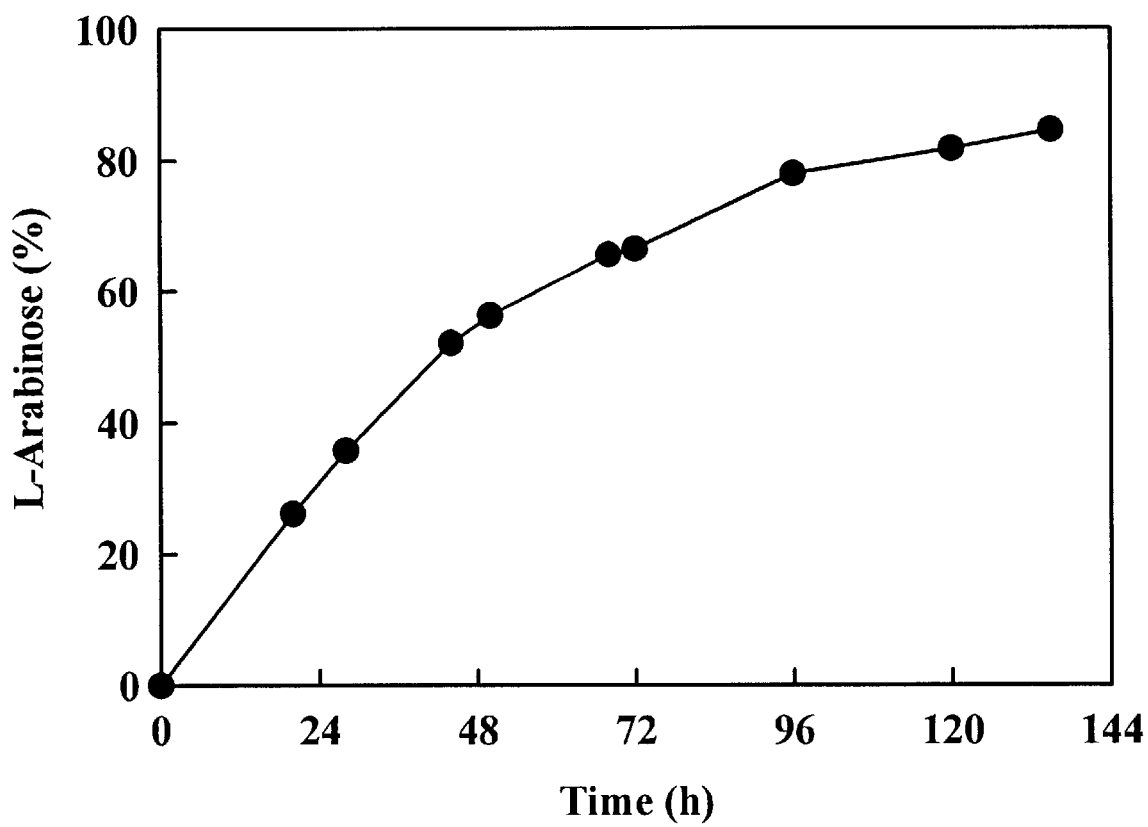
FIG. 4. Time course of arabinan (1%, w/v) hydrolysis by purified α-L-arabinofuranosidase (0.445 U/ml) from *A. pullulans* Y-21792 at pH 4.5 and 50° C.
Figure 5B:
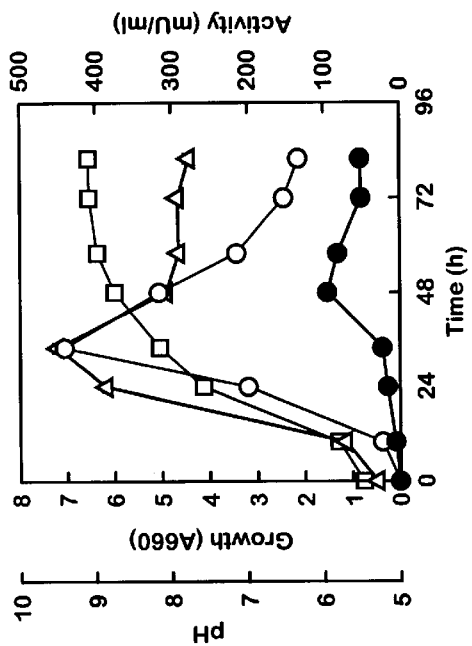
FIGS. 5A–D. Time courses of α-L-arabinofuranosidase production by *Aureobasidium pullulans* Y-21792 grown on (A) L-arabinose, (B) L-arabitol, (C) beet sugar arabinan and (D) wheat arabinoxylan (each, 1%, w/v) at 28° C. Symbols: □, pH; △, growth ($A_{660}$); ○, whole broth α-L-arabinofuranosidase activity; ●, extracellular α-L-arabinofuranosidase activity. Values are averages from duplicate experiments.
Figure 5D:
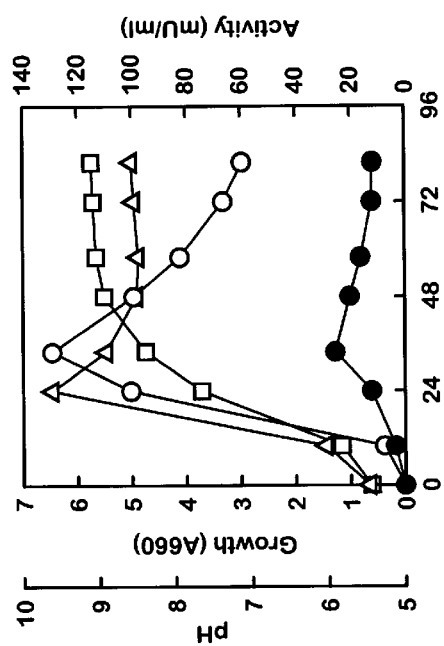
Figure 5A:
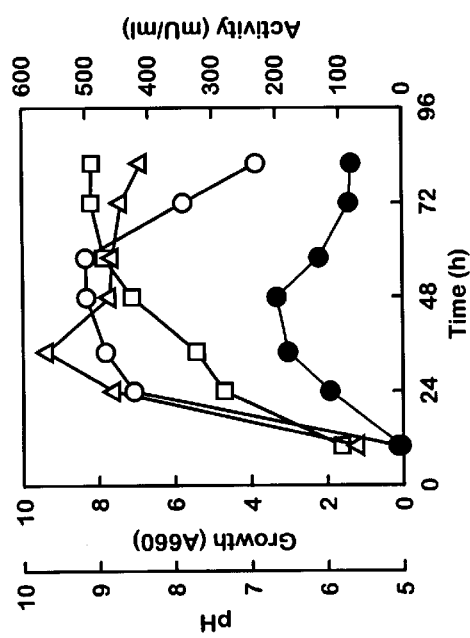
Figure 5C:
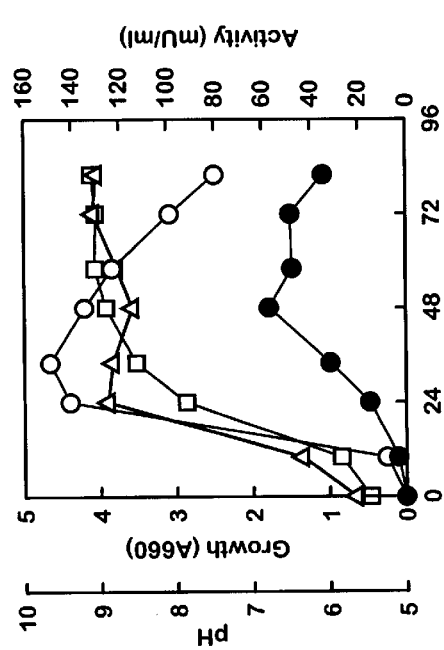

Hydrolysis of arabinan, debranched arabinan and arabinoxylans. The degradation of arabinan by α-L-AFase was followed by analyzing the reaction product by HPLC. Only arabinose was detected in the reaction product. Arabinan (1%, w/v; L-arabinose: galactose: rhamnose: galacturonic acid, 88: 3: 2: 7) was completely hydrolyzed by the purified enzyme (0.445 U/ml) (FIG. 4). Debranched arabinan (1%, w/v, L-arabinose: galactose: rhamnose: galacturonic acid, 88: 4: 2: 6) was also readily hydrolyzed by the α-L-AFase. The $K_m$ values for the degradation of arabinan and debranched arabinan were 2.14 and 3.25 mg/ml and $V_{max}$ values were 14.7 and 11.5 $\mu$mole.$min^{-1}$.$mg^{-1}$ protein, respectively. The arabinose released from arabinan and debranched arabinan (each at 1%. w/v) by the enzyme were 0.145 and 0.13 mg/ml, respectively, in 18 h at pH 4.5 and 50° C. using 0.3 U enzyme per ml reaction mixture. Arabinose was detected by HPLC analysis as a product from wheat arabinoxylan, rye arabinoxylan, oat spelt xylan and birch wood xylan. The arabinose release from wheat arabinoxylan, rye arabinoxylan, oat spelt xylan and birch wood xylan (each at 1%. w/v) by the enzyme were 0.8, 1.4, 0.25 and 0.56 mg/ml, respectively in 60 h at pH 4.5 and 50° C. using 0.3 U enzyme per ml reaction mixture. However, no arabinose was detected in arabinogalactan hydrolysis by the α-L-AFase.

Discussion

This is the first report to our knowledge on the purification and characterization of α-L-AFase from a color variant strain of *A. pullulans*. Also, this is the first α-L-AFase reported to have such a high thermophilicity. The extracellular α-L-AFase was purified 232-fold from the oat spelt xylan grown cell-free culture broth by a combination of ammonium sulfate treatment, DEAE Bio-Gel A agarose column chromatography, Bio-Gel A-0.5m gel filtration, arabinan-Sepharose 6B affinity chromatography and SP-Sephadex C-50 column chromatography (Table 1). The purification results suggest that the enzyme preparation from *A. pullulans* strain NRRL Y-21792 contains only one form of α-L-AFase as no other active peak was detected during each purification step. Multiple forms of α-L-AFase have been detected in the culture broth of *Aspergillus nidulans* (Ramon et al., 1993, J. Biotechnol., 113:15–22), A. niger (Rombouts et al., 1988, Carbohydr. Polym., 9:25–47), *A. terreus* (Luonteri et al., 1995, J. Biotechnol., 38:279–291) and *Penicillium capsulatum* (Filho et al., 1996, Appl. Environ. Microbiol., 62:168–1783). The specific activity of α-L-AFase from *A. pullulans* NRRL Y-21792 was 21.48 U/mg protein at pH 4.5 and 75° C.

The α-L-AFase from *A. pullulans* is a homodimer with a native molecular weight (MW) of 210,000 and a subunit MW of 105,000. Work by Komae et al. (1982, Agric. Biol. Chem., 46:1899–1905) showed that the MW of (α-L-AFase from *Streptomyces purpurascens* IFO 3389 was about 495, 000 and it contained 8 equal subunits of MW of 65,000. The MW of α-L-AFase of *Butyrivibrio fibrisolvens* GS113 was 240,000 and it consisted of 8 subunits of MW 31,000 (Hespell and O'Bryan, ibid). The α-L-AFase from *Clostridium acetobutylicum* ATCC 824 was a single polypeptide with a MW of 94,000 (Lee and Forsberg, ibid). The intracellular α-L-AFase from *A. niger* was a monomer with a MW of 67,000 (Kaneko et al., 1993, Biosci. Biotech. Biochem., 57:1161–1165). Thus, there is considerable diversity in enzyme structure for different microbial α-L-AFases. The maximal activity of the purified α-L-AFase from A.

*pullulans* was observed at 75° C. and pH 4.0–4.5 (FIGS. 2 and 3). Other microbial α-L-AFases have a broad range of pH and temperature dependence, with optimum activity occurring between pH 3.0–6.9 and 40°–70° C. (Bezalel et al., ibid; Fernandez-Espinar et al., 1994, FEMS Microbiol. Letts., 115:107–112; Filho et al., ibid; Kaji, 1984, Adv. Carbohydr. Chem. Biochem., 42:383–394; Lee and Forsberg, ibid). The purified enzyme from *Rhodotorula flava* is highly acid stable, retaining 82% of its activity after being maintained for 24 h at pH 1.5 and at 30° C., and has an optimum activity at pH of 2.0 (Uesaka et al., 1978, J. Bacteriol., 133:1073–1077). To our knowledge, the purified α-L-AFase from *A. pullulans* is the most thermostable enzyme reported to date with a half-life of 8 h at 75° C. and an optimum temperature of 75° C. Therefore, the thermophilic characteristic of the α-L-AFase from the mesophilic yeast-like fungus *A. pullulans* makes it suitable for use in commercial hemicellulose saccharification processes operating at elevated temperatures.

The purified α-L-AFase from *A. pullulans* hydrolyzed pNPαAF, arabinan and debranched arabinan, and released arabinose from wheat and rye arabinoxylans and oat spelt and birch wood xylans. In contrast to the α-L-AFases from *A. niger* (Kaji and Tagawa, 1970, ibid) and *S. purpurascens* IFO 3389 (Komae et al., ibid) which hydrolyze either (1→5) or (1→3)-arabinosyl linkages, the purified α-L-AFase from *A. pullulans* released only arabinose from α-(1→3)-arabinoxylans, arabinan, and debranched α-(1→5)- arabinan. From these results, it is concluded that the α-L-AFase from *A. pullulans* has hydrolytic activity for both α-(1→3) and α-(1→5)-linked, non-reducing, terminal L-arabinofuranose residues, and does not act on internal α-L-arabinosyl linkages. These properties are similar to the substrate specificity of other α-L-AFase from Streptomyces sp. strain 17-1 (Kaji et al., 1981, Agric. Biol. Chem., 45:925–931), *Streptomyces diastaticus* (Tajana et al., ibid) and *Bacillus subtilis* 3–6 (Kaneko et al., 1994, Appl. Environ. Microbiol., 60__3425–3428). The enzyme purified from *S. purpurascens* was active on pNPαAF but inactive against arabinans and arabinogalactans (Komae et al., ibid). Kormelink et al. (1991, Appl. Microbiol. Biotechnol., 35:753–758) described another type of α-L-AFase that was active only on arabinoxylans. The α-L-AFase from *Streptomyces lividans* exhibited no activity against oat spelt xylan or arabinogalactan (Manin et al., ibid). It slowly acted on arabinan and arabinoxylans by releasing arabinose after prolonged incubation (overnight). The limit of hydrolysis of arabinan by the α-L-AFase from *B. subtilis* 3–6 was only 15%, even when the enzyme was present in excess (Kaneko et al., 1994, ibid).

It is interesting that the α-L-AFase from *A. pullulans* had very little activity (3.4%) on p-nitrophenyl-α-L-arabinopyranoside. No significant α-glucosidase, β-galactosidase, β-glucosidase, β-xylosidase or cellobiosidase activity was associated with the purified α-L-AFase. The α-L-AFase from *A. pullulans* was not inhibited by 8 mM pNPαAF or with 1.2M (21.6%) L-arabinose in the reaction mixture. One α-L-AFase from *P. capsulatum* was competitively inhibited by L-arabinose with a $K_i$ of 16.4 mM (Filho et al., ibid). L-Arabinose at 80 mM concentration caused a 40% reduction of the hydrolytic activity of α-L-AFase from *A. nidulans* (Fernandez-Espinar et al., ibid). None of the metal ions tested stimulated or inhibited α-L-AFase activity. Enzyme inhibition was not observed in the presence of EDTA. These results suggest that no metals are needed for the enzymatic reaction. The α-L-AFase activity was not inhibited by DTT or the thiol-specific inhibitor (pCMB) indicating that disulfide bonds are not critical for enzyme activity. The α-L-AFases from *A. nidulans* (Fernandez-Espinar et al, ibid), *Ruminococcus albus* (Greve et al., ibid), *B. fibrisolvens* (Hespell and O'Bryan, ibid), Streptomyces sp. strain 17-1 (Kaji et al., 1981, ibid) and *S. purpurascens* (Kaneko et al., 1993, ibid) were all sensitive to sulfhydryl reagents.

The high activity of the α-L-AFase from *A. pullulans* on both arabinan and debranched arabinan, its ability to release L-arabinose from arabinoxylans, and its high thermostability and activity make the enzyme particularly suitable for use in the production of fermentable sugars from hemicellulosic biomass such as corn fiber and to improve animal feed digestibility by hydrolyzing arabinoxylans, a major component of animal feed (Campbell and Bedford, 1992, Can. J. Anim. Sci., 72:449–466).

EXAMPLE 2

The *A. pullulans* strain NRRL Y-21792 of Example 1 was examined to determine the effect of different carbon sources on α-L-arabinofuranosidase production.
Materials and Methods Materials. The color variant strain NRRL Y-21792 of *A. pullulans* was obtained from the ARS culture collection, NCAUR, Peoria, Ill., as in Example 1. Arabinogalactan, all saccharides and all aryl-glycosides were purchased from Sigma Chemical Co., St. Louis, Mo. Arabinan (beet sugar) and wheat arabinoxylan were purchased from MegaZyme, North Rocks, Australia.

Medium and enzyme production. The media used for seed culture and enzyme production were prepared as described in Example 1 with the exception of the particular carbon source. The carbon sources which were used are shown in Table 2. The shake flasks (125-ml Erlenmeyer flask containing 50 ml medium) were inoculated with 2 ml of seed culture (prepared using L-arabinose as carbon source) and cultivated on a rotary shaker (200 rpm) at 28° C. for 4 days. At intervals, ~2 ml of the whole culture broth were withdrawn, and the cells and unutilized insoluble substrates were removed from the culture broth by centrifugation (18,000×g, 20 min).

Analytical procedures. α-L-AFase activity was assayed as described in Example 1. Cell growth was monitored by measuring optical density of the culture broth at 660 nm ($A_{660}$).
Results and Discussion The effect of carbon sources on growth and α-L-AFase production by *A. pullulans* NRRL Y-21792 in shake flasks was investigated (Table 2). It grew and produced α-L-AFase activity on every substrate tested. The amount of α-L-AFase was largely dependent on the carbon source used by the organism for growth. As shown in Table 2, L-arabinose was the most effective carbon source for production of both whole culture broth (assayed without breaking the cells) and extracellular α-L-AFase activity, followed by L-arabitol. However, only 40 and 22% of the whole culture broth activity are extracellular in the case of L-arabinose and L-arabitol-grown cultures, respectively. About 70% of the α-L-AFase activity was extracellular in xylose grown cultures. Oat spelt xylan, sugar beet arabinan and wheat arabinoxylan were intermediate in their ability to support production of α-L-AFase. Lower amounts of enzyme activity were detected in corn fiber and arabinogalactan grown cultures. Time courses of α-L-AFase production by *A. pullulans* grown on L-arabinose, L-arabitol, beet sugar arabinan and wheat arabinoxylan are shown in FIGS. 5A–D. Generally, α-AFase production increased sharply up to 24–48 h, after which activity declined. Our results indicate that L-arabinose was the best inducer of α-L-AFase production, followed by L-arabitol. Arabinan and arabinoxylans could not induce the enzyme production to that extent. In comparison, the greatest amount of α-L-AFase was found in the culture fluid of *Streptomyces purpurascens* by using sugar beet arabinan as a carbon source (Komae et al., 1982, ibid). L-arabitol was the best inducer for production of extracellular α-L-AFase activity in *Aspergillus niger* (Veen et al., 1993, Arch. Microbiol., 159:66–71) and also in *A. nidulans* (Ramon et al., 1993, FEMS Microbiol. Letts., 113:15–22). In *Butyrivibrio fibrisolvens* GS 113, about 10% of the enzyme activity was extracellular (Hespell and O'Bryan, ibid). The α-L-AFase from *A. pullulans* is the first enzyme the production of which is induced best by L-arabinose. The low cost production of the α-L-AFase from *A. pullulans* would be of interest for the application of the enzyme in the saccharification of various hemicellulosic residues to fermentable sugars for the subsequent production of fuel ethanol and value added chemicals.

It is understood that the foregoing detailed description is given merely by way of illustration and that modifications and variations may be made therein without departing from the spirit and scope of the invention.

TABLE 1

Purification of α-L-arabinofuranosidase from *A. pullulans* Y-21792

| Step | Total protein (mg) | Total activity (U) | Specific activity (U/mg protein) | Recovery (%) | Purification fold |
|---|---|---|---|---|---|
| Culture supernatant | 2373 | 91 | 0.04 | 100 | 0 |
| Ammonium sulfate | 772 | 72 | 0.09 | 79 | 2.5 |
| DEAE Bio-Gel A agarose | 166 | 57.5 | 0.35 | 63 | 9 |
| Bio-Gel A-0.5m | 10.6 | 22.5 | 2.12 | 25 | 56 |
| Arabinan-Sepharose 6B | 2.2 | 12.3 | 5.68 | 14 | 151 |
| SP-Sephadex C-50 | 1.2 | 10.3 | 8.59 | 11 | 232 |

Table 2

Effect of carbon source on growth and α-L-arabinofuranosidase production by *Aureobasidium pullulans* Y-21792[a]

| Carbon source (1%,w/v) | Growth ($A_{660}$) | L-arabinosidase (mU/ml culture) | |
|---|---|---|---|
| | | Whole broth | Supernatant |
| Arabinan (sugar beet) | 3.9 | 149 (34) | 57 (48) |
| Arabinoxylan (wheat) | 5.5 | 129 (34) | 25 (34) |
| Arabinogalactan | 3.1 | 45 (34) | 9 (34) |
| L-Arabinose | 7.6 | 500 (58) | 199 (48) |
| L-Arabitol | 7.2 | 441 (34) | 95 (48) |
| Xylose | 8.0 | 129 (48) | 88 (48) |
| Xylitol | 9.1 | 94 (48) | 47 (58) |
| Oat spelt xylan | — | 159 (48) | 44 (48) |
| Corn fiber | — | 47 (48) | 22 (48) |

[a] Values reported are averages from duplicate experiments for each substrate. Cultures were grown in 125 ml Erlenmeyer flasks containing 50 ml medium at 28° C. for 96 h. The figures in parenthesis indicates the time of maximum enzyme production during the time course study.
-, not determined.

We claim:

1. A substantially pure thermostable α-L-arabinofuranosidase produced by *Aureobasidium pullulans* NRRL Y-21792 and which is isolated from cells thereof, said α-L-arabinofuranosidase having maximal activity at 75° C. being effective for the hydrolysis of arabinofuranosyl residues from L-arabinose containing polysaccharides and hemicelluloses.

2. The α-L-arabinofuranosidase of claim 1 which is homogeneously pure.

3. A composition comprising the α-L-arabinofuranosidase of claim 1 free from cells of said *Aureobasidium pullulans* NRRL Y-21792 and an inert carrier.

4. A method for hydrolyzing an L-arabinose-containing hemicellulosic material comprising contacting said hemicellulosic material with the α-L-arabinofuranosidase of claim 1 in an amount and under conditions effective to produce L-arabinose from said hemicellulosic material.

5. The method of claim 4 further comprising contacting said hemicellulosic material with a xylanolytic enzyme in an amount and under conditions effective for hydrolyzing said hemicellulosic material to produce xylose.

6. The method as described in claim 5 wherein said hemicellulosic material is contacted with said α-L-arabinofuranosidase and said xylanolytic enzyme sequentially.

7. The method as described in claim 4 wherein said hemicellulosic material comprises a lignocellulosic biomass.

8. The method as described in claim 7 further comprising subjecting said lignocellulosic biomass to a pretreatment effective to solubilize hemicellulose in said biomass or to increase the accessible surface area of hemicellulose, or both, prior to said contacting with said α-L-arabinofuranosidase.

9. The method as described in claim 8 wherein said pretreatment is selected from the group consisting of treatment with acid, treatment with alkali, ammonia fiber explosion, treatment with an organic solvent, autohydrolysis by steam explosion, acid steam treatment, treatment with hot, compressed liquid water, pressure cooking, milling, grinding, shearing, and extruding.

10. The method as described in claim 7 wherein said lignocellulosic material is selected from the group consisting of agricultural residues, wood, municipal solid wastes, paper and pulp industry wastes, and herbaceous crops.

11. A method for producing ethanol comprising hydrolyzing an L-arabinose-containing hemicellulosic material by contacting said hemicellulosic material with the α-L-arabinofuranosidase of claim 1 in an amount and under conditions effective to produce L-arabinose from said hemicellulosic material and fermenting said L-arabinose to ethanol.

12. The method as described in claim 11 wherein the hydrolysis of said hemicellulosic material to produce L-arabinose and the fermentation of said L-arabinose to ethanol are conducted simultaneously.

13. The method as described in claim 11 wherein the hydrolysis of said hemicellulosic material to produce L-arabinose and the fermentation of said L-arabinose to ethanol are conducted sequentially.

* * * * *